United States Patent [19]

Solomon et al.

[11] Patent Number: 5,015,238

[45] Date of Patent: May 14, 1991

[54] EXPANDABLE OBTURATOR AND CATHETER ASSEMBLY INCLUDING SAME

[75] Inventors: Donald D. Solomon, Spring Valley; Mutlu Karakelle, Dayton; Richard W. Beck, Centerville, all of Ohio

[73] Assignee: Becton, Dickinson and Company, Franklin Lakes, N.J.

[21] Appl. No.: 409,856

[22] Filed: Sep. 20, 1989

Related U.S. Application Data

[63] Continuation of Ser. No. 369,430, Jun. 21, 1989, abandoned.

[51] Int. Cl.$^5$ ................................................ A61M 5/00
[52] U.S. Cl. ...................................... 604/164; 604/265
[58] Field of Search .................... 604/265, 164, 890.1, 604/170, 280; 128/772, 657, 658

[56] References Cited

U.S. PATENT DOCUMENTS

| | | | |
|---|---|---|---|
| 3,572,333 | 3/1971 | Hubert et al. | |
| 3,695,921 | 10/1973 | Shepherd et al. | 427/2 |
| 4,515,593 | 5/1985 | Norton | 604/265 |
| 4,526,579 | 7/1985 | Ainpour | 604/265 |
| 4,647,643 | 3/1987 | Zdrahala et al. | |
| 4,668,221 | 5/1987 | Luther | |
| 4,743,629 | 5/1988 | Karakelle et al. | |

OTHER PUBLICATIONS

Barbara A. Brown, *Hematology: Principles and Procedures*, Lea & Febiger 1984.

*Primary Examiner*—Stephen C. Pellegrino
*Attorney, Agent, or Firm*—Richard E. Brown

[57] ABSTRACT

An oburator includes a solid substantially stiff rod of a nonhydrophilic polymer coated with a layer of a hydrophilic polyurethane which may have an antithrombogenic agent bulk distributing therein. When the hydrophilic polyurethane comes into contact with an aqueous liquid such as water, saline or a body fluid, it absorbs the liquid and expands thereby enlarging the diameter of the obturator. Another aspect of the invention is an assembly of a catheter and the obturator of the invention. When the obturator is emplaced in the catheter and brought into contact with a liquid, it expands, releases the antithrombogenic agent and contacts the lumen wall of the catheter thereby forming a seal which prevents backflow of a body fluid.

24 Claims, 2 Drawing Sheets

EXPANDABLE OBTURATOR AND CATHETER ASSEMBLY INCLUDING SAME

This application is a continuation of application Ser. No. 07/369,430, filed June 21, 1989, now abandoned.

BACKGROUND OF THE INVENTION

1. Field of the Invention

This invention relates to catheterization of a patient, and more particularly relates to an obturator assembly which prevents backflow of blood or other body fluid during a catheterization procedure.

2. Background of the Invention

For many applications, a catheter, after insertion into a patient, must be maintained in place for periods up to two weeks or more. During this time, medication changeovers may be alternated with periods when no solutions are being administered to the patient. It is essential that patency of the catheter be maintained during changeover periods.

In the current state of the art, patency of a vascular access catheter, with or without an attached intravenous drip, is generally maintained in one of three ways. A sterile aliquot of heparin solution may be injected into the catheter. This method, often termed a heparin lock, is costly since expensive heparin may be required for prolonged periods. Alternatively, a sterile bolus of normal saline solution may be injected into the catheter. Both of these methods must be done routinely and often; however, because of normal diffusion at the tip of the catheter, blood may replace infused heparin or saline solutions. A common result is the loss of patency through the formation of a clot near the tip of the catheter. In a third method for maintenance of patency, a stainless steel or plastic obturator may be inserted loosely inside the catheter and attached with a leur connector. These devices are primitive and do not completely seal the catheter so that blood may seep back into the space between the catheter and obturator. This backflow of blood not only may clot and occlude the catheter or interfere with subsequent removal of the obturator, but also is an excellent breeding ground for infection.

Hydrophilic polymers which absorb water and expand, often termed hydrogels, have long been known. Karakelle et al., in U.S. Pat. No. 4,743,629 discloses hydrophilic polyurethane compositions which absorb significant amount of water, expand and allow species soluble in water to permeate through the composition by a partition type permeability process.

Hydrophilic polyurethanes which absorb water and expand have been used to manufacture over-the-needle catheters. These catheters are emplaced in a patient's vein by mounting the catheter by a press fit over a needle or catheter inserter used to puncture the vein. The catheter, due to its hydrophilic nature absorbs water so that its diameter expands releasing the needle and leaving the catheter emplaced and ready for administration of a solution. Exemplary of such over the needle catheters is the disclosure of Luther in U.S. Pat. No. 4,668,221. Luther does not, however, address the problem of maintaining patency of the patented catheter after removal of the needle.

A definite need exists in the art for a reliable, improved and inexpensive method to maintain patency in an indwelling catheter during medication changeovers. The present invention addresses this need.

SUMMARY OF THE INVENTION

The invention provides an obturator which includes a substantially stiff nonhydrophilic rod coated with a substantially hydrophilic polyetherurethane (hereinafter referred to as HPEU) capable of absorbing a liquid and increasing the diameter of the obturator. Preferred obturators of the invention include a medicinal agent, such as an antithrombogenic and/or antiinfective agent, bulk distributed in the HPEU. (In the present disclosure, the term bulk distributed means evenly distributed throughout the entire HPEU layer of the obturator.) These medicinal agents are slowly released by a sustained or controlled release mechanism thus providing efficacy over the intended period of use of the device.

The HPEU of the invention may be the reaction product of a diisocyanate, polyglycol and chain extender. The most preferred HPEU is the reaction product of 4,4'-diphenylmethane diisocyanate (MDI), polyethyleneoxide glycol (PEG) and 1,4-butanediol (BDO) having heparin bulk distributed therein.

Another aspect of the invention is an assembly which includes the obturator of the invention and a catheter. In a preferred assembly of the invention, the catheter includes a radiopaque agent, preferably as a stripe or layer.

When the obturator of the assembly of the invention is wetted by an aqueous liquid, the HPEU absorbs water, releases the antithrombogenic agent, and expands so that the obturator increases in diameter and contacts the lumenal wall of the catheter to form a seal. Thus, with the assembly of the invention, backflow of a body fluid, such as blood, into an emplaced catheter may be prevented safely and effectively without resort to a conventional heparin lock, which is costly when patency of the emplaced catheter must be maintained for a prolonged period of time. Further, variations in inside diameter are common within a given gauge size among catheters produced by various manufacturers or even, to a lesser extent, from lot to lot for a single manufacturer. The expandable obturator of the invention works well to seal all catheters within a given gauge size.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

In accordance with the present invention, there is provided a coated obturator which includes a rod coated with an HPEU. The HPEU, when contacted with an aqueous liquid, absorbs water so that the coated obturator increases in outside diameter. When inserted into an indwelling catheter, the expansion causes the coating of hydrophilic polymer to contact and form a seal with the lumenal wall of the catheter. At the same time, sodium heparin or a complex of tridodecylmethyl ammonium chloride and heparin (hereinafter TDMAC-heparin), bulk distributed in the HPEU, is slowly released during the use of obturator thus providing antithrombogenic activity. The seal, while sufficiently tight to prevent backflow of a body fluid into the catheter, is nevertheless loose enough that the obturator may easily be withdrawn from the catheter.

Figure 1:
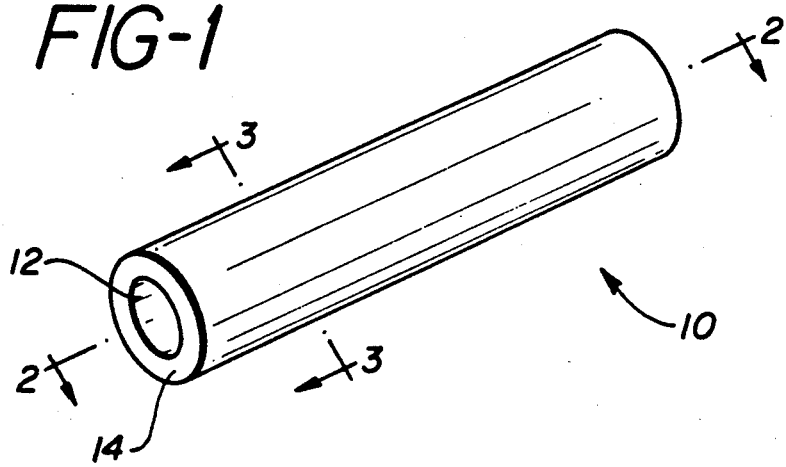
FIG. 1 is a perspective view of the preferred coated obturator of the invention.
Figure 2:
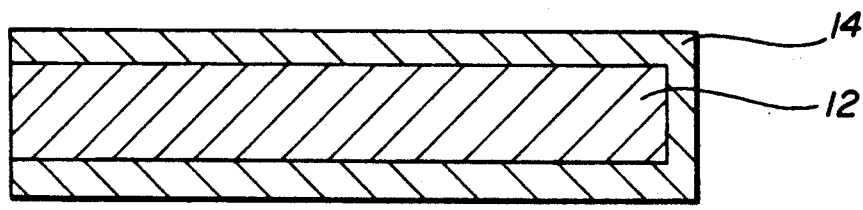
FIGS. 2 and 3 are sectional views of the coated obturator of FIG. 1 taken along the lines 2—2 and 3—3 respectively thereof.
Figure 3:
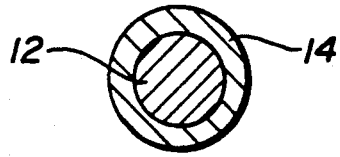
Figure 4:
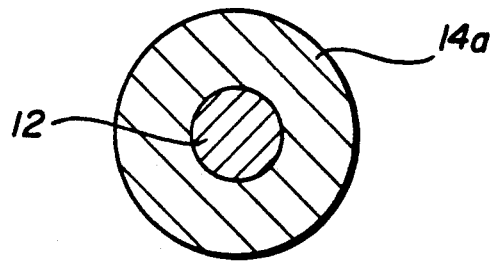
FIG. 4 is a sectional view corresponding to FIG. 3 after swelling of the coated obturator.

Adverting now to the drawings, FIGS. 1-3 illustrate a coated obturator 10 of the invention including a rod 12 and a coating 14 of hydrophilic polymer. The hydrophilic polymer coating 14 expands to coating 14a when it come into contact with water, as shown in FIG. 4.

Figure 5:
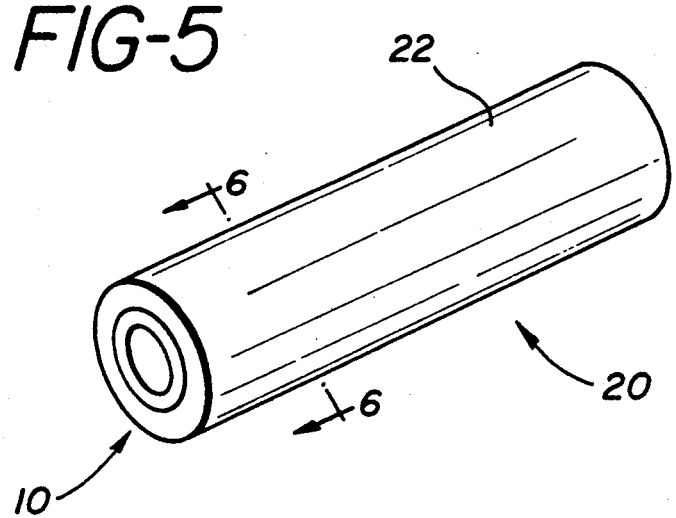
FIG. 5 is a perspective view of the catheter assembly of the invention including the coated obturator of FIG. 1.
Figure 6:
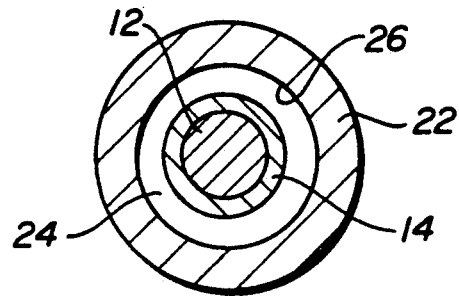
FIG. 6 is an enlarged sectional view of the assembly of FIG. 5 taken along the line 6—6 thereof.
Figure 7:
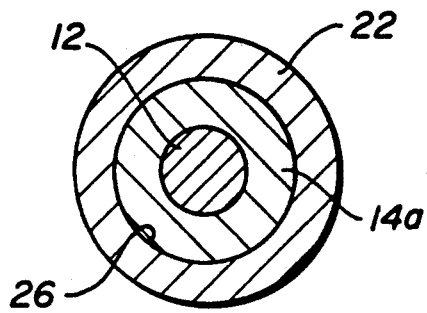
FIG. 7 is a sectional view of the assembly of FIG. 5 after swelling of the coated obturator.

FIGS. 5-7 illustrate a catheter assembly 20 which includes a catheter 22 having the coated obturator 10 positioned therein. FIGS. 6 and 7 show the relationship of coated obturator 10 to catheter 22 before and after the obturator is wetted with water respectively. It is readily seen from FIG. 6 that prior to wetting the coated obturator, it slides within catheter 22 so that there is a gap 24 between coating 14 and the lumenal wall 26 of catheter 22. After wetting with water, the expanded hydrophilic coating 14a substantially fills gap 24 and contacts wall 26, as illustrated in FIG. 7.

The rod may be of any substantially nonhydrophilic material which, when extruded, is substantially stiff and retains its stiffness when immersed in water. Suitable materials are, for example, metal, such as stainless steel, or, preferably, a polymer. Preferred polymers for the rod are polyolefins, such as polyethylene, polypropylene, and polytetrafluoroethylene, polyester, polyamide, polystyrene, polyvinylchloride and liquid crystal polymers.

The HPEU coated onto the rod includes three essential ingredients, a diisocyanate, PEG and a chain extender. Other components may be included as described below.

Suitable diisocyanates are aromatic diisocyanates such as MDI, 3,3'-diphenylmethane diisocyanate, alicyclic diisocyanates such as isophorone diisocyanate, and 4,4'-dicyclohexylmethane diisocyanate, and aliphatic diisocyanates, as, for example, hexamethylene diisocyanate. The most preferred diisocyanate is MDI. Other diisocyanates which may be used include fluorine substituted isocyanates and silicones containing isocyanate groups.

The polyether glycol component may be PEG, having a molecular weight of about 600 to 16,000, preferably about 1,000 to 10,000. The most preferred PEG has a molecular weight 1,450. The PEG may be used alone or mixed with from 0 to 50% by weight of another polyglycol. Suitable polyglycols which may be mixed with the PEG include polypropyleneoxide glycol, polytetramethyleneoxide, (PTMO) glycol and a silicone glycol. Silicone glycols and PTMO are substantially hydrophobic, and by mixing a suitable quantity of these glycols with the PEG, the degree of hydrophobicity of the HPEU may be tailored according to the desired extent of expansion. Silicone glycols are well-known, and representative examples are described in U.S. Pat. No. 4,647,643 to Zdrahala et al. A particularly useful silicone glycol is commercially available from Dow Corning Corp. under the destination 4-3667 fluid (formerly Q4-3667).

The chain extender may be water and/or a low molecular weight branched or unbranched diol, diamine or aminoalcohol of up to 10 carbon atoms or mixtures thereof. Representative nonlimiting examples of chain extenders are BDO; ethylene glycol; diethylene glycol; triethylene glycol; 1,2-propanediol; 1,3-propanediol; 1,6-hexanediol; 1,4-bis-hydroxymethyl cyclohexane, hydroquinone dihydroxyethyl ether, ethanolamine, ethylenediamine and hexamethylenediamine. Preferred chain extenders are 1,6-hexanediol, ethylenediamine, hexamethylenediame and, most preferably, water and BDO.

In addition to the above-described essential ingredients, the HPEU may include about 0 to 10% by weight of a crosslinking agent. The crosslinker may be a low molecular weight multifunctional compound having three or more hydroxyl and amine groups and 10 or less carbon atoms. Representative suitable crosslinkers are trimethylolpropane (TMP), glycerol, pentaerythritol, trimethylolethane, mannitol and the like. Preferred crosslinkers are triols, most preferably TMP.

The percentages of the components may be such that the soft segment of the HPEU may be from about 20 to 80, preferably from about 55 to 70% of the total weight of the formulation. From the predetermined percentage of hard segment, the proportions of the components may readily be calculated.

The HPEU of the invention may be prepared by a solution polymerization procedure. The hydroxyl-containing components (PEG, polyglycol, extender, crosslinker) may be combined in an aliquot of a suitable solvent, as for example dimethylacetamide (DMAC) and the diisocyanate dissolved in another aliquot of the solvent. The two aliquots may be combined and maintained at a suitable temperature, with stirring for a sufficient time to complete the polymerization. A typical procedure is given in Example I and representative HpEUs are listed in the Table.

An alternative method to prepare the HPEU of the invention is to combine all the ingredients together at one time without a solvent. This procedure is known in the art as one-shot or bulk polymerization.

Synthesis of hydrophilic polyurethanes is generally carried out with a catalyst. However, a feature of the method of the invention is that the HPEU is prepared from the components without adding a polymerization catalyst. Conventional catalysts in the art, for example, organometallic compounds such as dibutyl tin dilaurate, are leachable and may cause deleterious effects in blood-contacting elements. By avoiding use of a catalyst, the HPEU of the invention is potentially purer and less toxic than those of the prior art.

The preferred coated obturator of the invention includes an antithrombogenic agent associated with the HPEU coating. Suitable antithrombogenic agents are prostaglandins, urokinase, streptokinase, tissue plasminogen activator and heparinoids wherein the term heparinoid includes heparin and salts and complexes thereof. Preferred antithrombogenic agents are sulfonated heparinoids, such as dextran sulfonate or most preferably heparin or a suitable heparin salt such as the sodium, potassium or ammonium salt.

In one method to prepare the coated obturator, sodium heparin may be suspended in a solvent solution of the HPEU. The rod may then be dipped in the solution or drawn through a mandrel containing the solution to form a coating on the rod. A suitable solvent for dissolving the HPEU is DMAC or, preferably DMAC and propylene glycol methyl ether acetate (PGMEA) mixed in a ratio of about 50:50 by volume.

The coated obturator may also be prepared by coextruding the polymer which forms the rod with the hydrophilic polymer containing bulk distributed heparin.

A preferred method for applying HPEU having bulk distributed heparin uses a solvent solution of sodium heparin containing emulsified HPEU. A solution containing about 20% by weight of sodium heparin in a mixture of about one part DMAC and about two parts water by volume may be added to a solution of about 12% by weight of HPEU in an about 7:1 mixture by volume of DMAC and water. On thorough mixing of these two solutions, an emulsion containing about 1 to 25, preferably about 10 to 20% by weight of total solids may be obtained. The rod may then be dipped into the emulsion to apply the HPEU-heparin coating and form the coated obturator of the invention. The HPEU-heparin coating may contain 1 to 25 preferably 5 to 15% by weight of sodium heparin in the dry form.

In a second preferred method to prepare the coated obturator of the invention, a complex of heparin with a quaternary salt may be used. Such complexes are well-known in the art and are described by McGary et al. in U.S. Pat. No. 4,678,660. Suitable complexes may be formed with cetylpyridinium chloride or benzalkonium chloride. Preferred complexes are those in which the heparin is complexed with dodecylmethyl ammonium chloride, or most preferably, with TDMAC. Application of the HPEU-heparin coating may be accomplished by dipping the rod into a solution containing about 5 to 50, preferably about 25% by weight of the HPEU and about 0.5 to 20, preferably about 2 to 8% by weight of the heparin complex in a suitable solvent or solvent combination. Exemplary of useful solvents are DMAC, DMF, N-methyl pyrrolidone, toluene, tetrahydrofuran, methyl ethyl ketone, petroleum ether, isopropanol and PGMEA. A preferred solvent is a 1:1 by volume mixture of DMAC and PGMEA.

In accordance with the coating methods described above, a coating of from 0.002 to 0.005 inches thick may be obtained on the polymeric rod.

The invention also contemplates bulk distribution in the HPEU layer of other medicinal agents, either alone or in conjunction with heparin. For example, an antibiotic or an antiinfective agent, such as chlorhexidine, silver sulfadiazine or other silver salts may be bulk distributed in the HPEU by the dipping process described above for heparin.

In another aspect of the invention, an assembly includes the coated obturator of the invention and a polymeric catheter. Any polymeric catheter as known in the art and used for vascular access may be included in the assembly of the invention. Suitable catheters are polyethylene, polypropylene, polyvinylchloride, polytetrafluoroethylene and preferably polyurethane catheters. The catheter of the invention may preferably have a conventional radiopaque agent associated therewith, preferably in the form of one or more stripes or layers of an agent such as barium sulfate, bismuth trioxide or a halogenated polyurethane. Alternatively, the radiopaque agent may be bulk distributed in the catheter.

The coated obturator of the invention is of constant diameter until it comes into contact with an aqueous liquid whereupon it may absorb from about 10 to 200, preferably about 50 to 150% by weight of water. Accordingly, for use in maintaining patency of an emplaced catheter, the coated obturator may be inserted into a catheter already having a bolus of normal saline in the lumen of the catheter, or the coated obturator may be dipped into an aqueous liquid, such as sterile normal saline and inserted into the catheter. The HPEU quickly absorbs the water, expands and contacts the lumen wall of the catheter. A seal is thereby formed which prevents backflow of blood or other body fluid. At the same time the water swollen HPEU heparin coating slowly releases its heparin or heparin-complex thus providing antithrombogenic activity. Alternatively, the coated obturator may be advanced through the catheter a sufficient distance that the forward end of the obturator projects beyond the end of the emplaced catheter to contact a body fluid. The obturator may then be retracted until it is inside the catheter, whereupon it expands due to absorbed body fluid to form the desired seal. After the obturator contacts the liquid and is in place in the catheter, the bulk distributed heparin or other medicament therein slowly migrates to the surface and is released to provide additional protection against thrombosis or infection.

The following Examples are provided to further describe the invention but are not to be considered as limitative of the invention:

EXAMPLE I

HPEU SYNTHESIS

A. Bulk Synthesis

Polyether was dried at 60° to 70° C. under vacuum (4 to 6 mm Hg) for 4 to 6 hours to remove moisture. Water content (Carl Fisher titration) and polyol hydroxyl number (phthalic anhydride-pyridine method) were determined to adjust formulation stoichiometry. MDI was filtered to remove any reacted diisocyanate and vacuum stripped (4 to 6 mm Hg) for 2 to 4 hours. The stoichiometric amounts of polyol and extender (BDO) were placed in the polymerization vessel and degassed at 60° C. for 30 minutes. Then, the stoichiometric amount of MDI (1.02 index) was added and stirred vigorously until the polymerization temperature reached about 85° to 90° C. The polymer was discharged and postcured at 125° C. for 30 minutes.

B. Solution Synthesis

Solution polymerization at 25% total solids was performed in DMAC under a nitrogen atmosphere. Polyether was dried at 60° to 70° C. under vacuum (4 to 6 mm Hg) for 4 to 6 hours to remove moisture. Water content (Carl Fisher titration) and polyol hydroxyl number (phthalic anhydride-pyridine method) were determined to adjust formulation stoichiometry. MDI was filtered to remove any reacted diisocyanate and vacuum stripped (4 to 6 mm Hg) for 2 to 4 hours. Stoichiometric amounts of polyether and extender (BDO) were placed in the polymerization vessel and degassed at 60° C. for 30 minutes. Two thirds of the DMAC was added to the polyol-extender mixture. The stoichiometric (1.02 Index) amount of the MDI was dissolved in the remaining DMAC and the solution was added dropwise to the polymerization vessel. The polymerization medium was maintained at 60° to 70° C. and constantly stirred. A polymerization time of four hours at 60° to 70° C. was sufficient for adequate polymer formation.

TABLE

HYDROPHILIC POLYETHERURETHANE (HPEU) FORMULATIONS

| FORMULATION NUMBER | HARD SEGMENT CONTENT (% WT) | POLYETHER TYPE | NUMBER OF EQUIVALENTS OF | | |
|---|---|---|---|---|---|
| | | | MDI | BDO | POLYOL |
| 1 | 30 | PEG 1450 | 1.02 | 0.506 | 0.494 |
| 2 | 35 | PEG 1450 | 1.02 | 0.597 | 0.403 |
| 3 | 40 | PEG 1450 | 1.02 | 0.667 | 0.333 |
| 4 | 45 | PEG 1450 | 1.02 | 0.738 | 0.262 |
| 5 | 50 | PEG 1450 | 1.02 | 0.772 | 0.228 |
| 6 | 55 | PEG 1450 | 1.02 | 0.821 | 0.179 |
| 7 | 60 | PEG 1450 | 1.02 | 0.845 | 0.155 |

MDI: 4,4'-Diphenylmethane diisocyanate (Mobay)
PEG 1450: Polyethylene glycol/MW = 1450 (Union Carbide)
BDO: 1,4-Butanediol (DuPont)

EXAMPLE II

Antithrombogenicity Study

TDMAC-heparin coatings on solid polymeric rods were prepared by dipping the rods into a DMAC solution containing 25% by weight of the HPEU of the invention and 2.5 and 5% by weight of a heparin-TDMAC complex. After solvent removal, the coated rods were dynamically leached in 1 l of 0.85% saline using an incubator shaker at 37° C. and 150 rpm for three days. Saline was changed daily and samples were removed every 24 hours to determine the antithrombogenicity by measuring the partial thromboplastin time (PTT) according to B. A. Brown, *Hematology Principles and Procedures*, Third Edition, Lea and Febiger Co. 1980. Noncoated control rods gave clotting times of from 25 to 40 seconds. Rods containing the 2.5 heparinized coating gave a PTT of greater than 1800 sec after 48 hours of leaching and 1000 sec after 72 hours. The rod containing a 5% heparinized coating gave a PTT of greater than 1800 sec after 72 hours.

What is claimed is:

1. An obturator comprising a substantially nonhydrophilic polymeric rod coated with an adhering substantially hydrophilic polyurethane having a medicinal agent bulk distributed therein said polyurethane being capable of absorbing a liquid, releasing said medicinal agent and expanding to form a seal when the coated rod is inserted into a catheter.

2. The obturator of claim 1 wherein said hydrophilic polyurethane comprises the reaction product of a diisocyanate, polyethyleneoxide glycol and a chain extender.

3. The obturator of claim 2 wherein said diisocyanate is selected from the group consisting of 4,4'-diphenylmethane diisocyanate, 3-3'-diphenylmethane diisocyanate, isophorone diisocyanate and hexamethylene diisocyanate.

4. The obturator of claim 2 wherein said chain extender is selected from the group consisting of 1,4-butanediol, ethylene glycol, diethylene glycol, triethylene glycol, 1,2-propanediol, 1,3-propanediol, 1,6-hexanediol, 1,4-bis-hydroxymethyl cyclohexane, hydroquinone dihydroxyethyl ether, ethanolamine, ethylenediamine and hexamethylenediamine.

5. The obturator of claim 2 wherein said polyethyleneoxide has a molecular weight of about 600 to 16,000.

6. The obturator of claim 2 wherein said hydrophilic polyurethane further comprises the reaction product of a polyglycol selected from the group consisting of polypropyleneoxide glycol, polytetramethyleneoxide glycol and a silicone glycol.

7. The obturator of claim 1 wherein said medicinal agent is selected from the group consisting of an antiinfective agent, an antibiotic and an antithrombogenic agent.

8. The obturator of claim 7 wherein said antithrombogenic agent is selected from the group consisting of a prostaglandin, urokinase, streptokinase, tissue plasminogen activator, heparin, a heparin salt and a complex of heparin with a quaternary salt.

9. An obturator comprising a substantially nonhydrophilic rod coated with an adhering substantially hydrophilic polyurethane, said hydrophilic polyurethane being capable of absorbing an aqueous liquid and expanding to form a seal when inserted into a catheter.

10. The obturator of claim 9 wherein said rod is selected from the group consisting of a metal rod and a polymeric rod.

11. The obturator of claim 10 wherein said polymeric rod is selected from the group consisting of a polyolefin, polytetrafluoroethylene, polyester, polyamide, polyvinyl chloride and liquid crystal.

12. An obturator comprising a substantially nonhydrophilic polyurethane rod and a coating thereon, said coating comprising a substantially hydrophilic polyurethane comprising the reaction product of 4,4'-diphenylmethane diisocyanate, polyethyleneoxide glycol and butanediol, said hydrophilic polyurethane having a heparinoid bulk distributed therein and being capable of absorbing a liquid, releasing said heparinoid and expanding to form a seal when inserted into a catheter.

13. An assembly comprising a polymeric catheter and an obturator dimensioned to fit therein, said obturator including a substantially nonhydrophilic polymeric rod having a coating thereon, said coating comprising a substantially hydrophilic polyurethane having a medicinal agent bulk distributed therein, said hydrophilic polyurethane being capable of absorbing a liquid, releasing said medicinal agent and expanding to form a seal when inserted into said catheter.

14. The assembly of claim 13 wherein said polymer is rod is selected from the group consisting of a polyolefin, polytetrafluoroethylene, polyester, polyamide, polyvinyl chloride and liquid crystal.

15. The assembly of claim 13 wherein said hydrophilic polyurethane comprises the reaction product of a diisocyanate, polyethyleneoxide glycol and a chain extender.

16. The assembly of claim 15 wherein said diisocyanate is selected from the group consisting of 4,4'- diphenylmethane diisocyanate, 3,3'-diphenylmethane diisocyanate, isophorone diisocyanate and hexamethylene diisocyanate.

17. The assembly of claim 15 wherein said chain extender is selected from the group consisting of 1,4-butanediol, ethylene glycol, diethylene glycol, triethylene glycol, 1,2-propanediol, 1,3-propanediol, 1,6-hexanediol, 1,4-bis-hydroxymethyl cyclohexane, hydroquinone dihydroxyethyl ether, ethanolamine, ethylenediamine and hexamethylenediamine.

18. The assembly of claim 15 wherein said polyethyleneoxide has a molecular weight of about 600 to 16,000.

19. The assembly of claim 15 wherein said hydrophilic polyurethane further comprises the reaction product of a polyglycol selected from the group consisting of polypropyleneoxide glycol, polytetramethyleneoxide glycol and a silicone glycol.

20. The assembly of claim 13 wherein said medicinal agent is selected from the group consisting of an antiinfective agent, an antibiotic and an antithrombogenic agent.

21. The assembly of claim 20 wherein said antithrombogenic agent is selected from the group consisting of a prostaglandin, urokinase, streptokinase, tissue plasminogen activator, heparin, a heparin salt and a complex of heparin with quaternary salt.

22. The assembly of claim 13 wherein said catheter includes a radiopaque agent.

23. An assembly comprising a polymeric catheter and an obturator dimensioned to fit therein, said obturator including a substantially nonhydrophilic rod coated with a substantially hydrophilic polyurethane, said hydrophilic polyurethane being capable of absorbing an aqueous liquid and expanding to form a seal when inserted into said catheter.

24. An assembly comprising a polymeric catheter and an obturator dimensioned to fit therein, said obturator including a substantially nonhydrophilic polymeric rod and a coating thereon, said coating comprising a substantially hydrophilic polyurethane comprising the reaction product of 4,4'-diphenylmethane diisocyanate, polyethyleneoxide glycol and butanediol, said hydrophilic polyurethane having a heparinoid bulk distributed therein and being capable of absorbing a liquid, releasing said heparinoid and expanding to form a seal when inserted into said catheter, said catheter including a radiopaque agent.

* * * * *